United States Patent [19]

Sahota

[11] Patent Number: 4,667,679
[45] Date of Patent: May 26, 1987

[54] APPARATUS AND METHOD FOR POSITIONING AND PUNCTURING AN ARTERY AND A VEIN

[76] Inventor: Harvinder Sahota, 3861 Wisteria, Seal Beach, Calif. 90740

[21] Appl. No.: 864,749

[22] Filed: May 13, 1986

Related U.S. Application Data

[63] Continuation of Ser. No. 644,026, Aug. 24, 1984, abandoned, which is a continuation-in-part of Ser. No. 407,508, Aug. 12, 1982, abandoned.

[51] Int. Cl.⁴ .............................................. A61B 10/00
[52] U.S. Cl. .................................... 128/663; 128/660; 604/116
[58] Field of Search .................. 128/660–663; 604/115–117

[56] References Cited

U.S. PATENT DOCUMENTS

| | | | |
|---|---|---|---|
| 1,561,116 | 11/1925 | Silliman | 604/115 |
| 1,824,516 | 9/1931 | Tyvand | 604/115 X |
| 2,103,174 | 12/1937 | Posada | 604/115 |
| 4,289,139 | 9/1981 | Enjoji et al. | 128/660 |
| 4,314,568 | 2/1982 | Loving | 604/116 X |
| 4,332,248 | 6/1982 | DeVitis | 604/117 X |
| 4,387,721 | 6/1983 | Enjoji | 128/661 X |
| 4,408,611 | 10/1983 | Enjoji | 604/116 X |
| 4,489,730 | 12/1984 | Jingu | 128/660 |
| 4,497,325 | 2/1985 | Wedel | 604/116 X |

FOREIGN PATENT DOCUMENTS

| | | |
|---|---|---|
| 1298707 | 12/1972 | United Kingdom . |
| 1462147 | 1/1977 | United Kingdom . |
| 1551345 | 8/1979 | United Kingdom . |
| 1568971 | 6/1980 | United Kingdom . |

*Primary Examiner*—Kyle L. Howell
*Assistant Examiner*—Angela D. Sykes
*Attorney, Agent, or Firm*—Knobbe, Martens, Olson & Bear

[57] ABSTRACT

A blood flow detector produces a signal in response to pulsatile blood flow to provide means for positioning a slot in a plate in alignment with a patient's artery. Pressing the plate against the patient's skin retains the artery in alignment with the slot for puncturing. A groove in the bottom of the plate holds the artery in position while a first slot located at one end of the groove is used to guide an instrument toward the artery. A second slot adjacent the first slot is spaced a predetermined distance from the first slot so that by guiding a needle through the second slot the vein corresponding to an artery can be penetrated.

10 Claims, 7 Drawing Figures

APPARATUS AND METHOD FOR POSITIONING AND PUNCTURING AN ARTERY AND A VEIN

CROSS REFERENCE TO RELATED APPLICATION

This application is a continuation of application Ser. No. 644,026, filed Aug. 24, 1984, abandoned, which is a continuation-in-part of the prior Application Ser. No. 407,508, filed Aug. 12, 1982, abandoned inventor Harvinder Sahota, entitled Apparatus and Method for Positioning and Puncturing an Artery.

BACKGROUND OF THE INVENTION

This invention is related to apparatus and methods for positioning and puncturing an artery preparatory to the insertion of a needle or catheter therein.

There are many situations which arise in medical practice, such as insertion of a catheter and withdrawal of blood, which require the puncturing of an artery with a needle or other similar device. Even experienced medical personnel sometimes have difficulty in positioning and puncturing an artery in some patients. It is particularly difficult to locate and puncture an artery in a patient who is obese because the arteries of such a person are not as close to the skin surfaces as the arteries in a person of normal weight. It is also often very difficult to locate and puncture an artery in a person who has very low blood pressure, which often occurs in persons who are extremely ill. Human arteries are normally two to eight millimeters in diameter; and some arteries may be difficult to locate even in a healthy person.

Prior methods for puncturing an artery include only means for determining the approximate position of the artery. Even after a medically trained person has found the patient's artery, puncturing the artery may be difficult, requiring more than one penetration of the patient's skin. In addition, difficulties are often encountered after the artery has been located since the insertion of the needle can cause the artery to roll away or be displaced as the surrounding body tissue is displaced.

Similar problems also arise when medical personnel attempt to locate and puncture a vein. Prior methods only allow medical personnel to determine the approximate location of a vein. Insertion of a needle or catheter can also cause the vein to roll away.

Therefore, there is a need in the art of medical instrumentation for a device which accurately identifies the location of a patient's artery or vein and which retains the artery or vein in position for puncturing.

SUMMARY OF THE INVENTION

Accordingly, the present invention includes means for emitting a signal in response to pulsatile changes in blood flow to ascertain the position of a selected artery and means for holding the artery in position for puncturing.

The signal emitting means is preferably a doppler detector of a type well known in the art for detecting blood flow. A signal processor processes the output signal of the doppler detector to provide a signal for driving a loudspeaker to provide an audible indication that the detector is adjacent an artery and a signal for operating a light which operates intermittently in response to pulsatile blood flow.

The invention includes a plate which provides means for mounting the doppler detector and the light. The plate includes at least one slot for alignment with an artery whose position the doppler detector ascertains. Pressing the plate against the patient's skin with a moderate pressure while an artery is in longitudinal alignment with the slot causes the artery to remain in position in alignment with the slot so that medical personnel may easily puncture the artery with a catheter needle or other similar needle.

The invention also includes a means for locating veins in the human body. A slot in the edge of the plate is spaced away from the slot which is in alignment with the artery. The slot is spaced from the slot a distance equal to the anatomical spacing between arteries and veins in the human body. Therefore, when the slot is located adjacent to the artery the slot in the edge of the plate is located over the vein which corresponds to the artery. The vein may then be punctured with a catheter needle or similar needle.

The invention is relatively inexpensive and easy to operate so that proficient use thereof requires little specialized training. The invention is useful to both highly trained medical personnel, such as physicians having experience in catheterization techniques, and to personnel, such as paramedicals, having a little experience in such techniques. In addition to being useful in locating an artery preparatory to insertion of a catheter, the invention is useful in positioning and puncturing an artery for withdrawing a blood sample and for other similar purposes. The invention is suitable for use with any patient and is particularly useful in puncturing the arteries of patients who have low blood pressure or whose arteries are not near the surface of the skin.

DESCRIPTION OF PREFERRED EMBODIMENT

Figure 1:
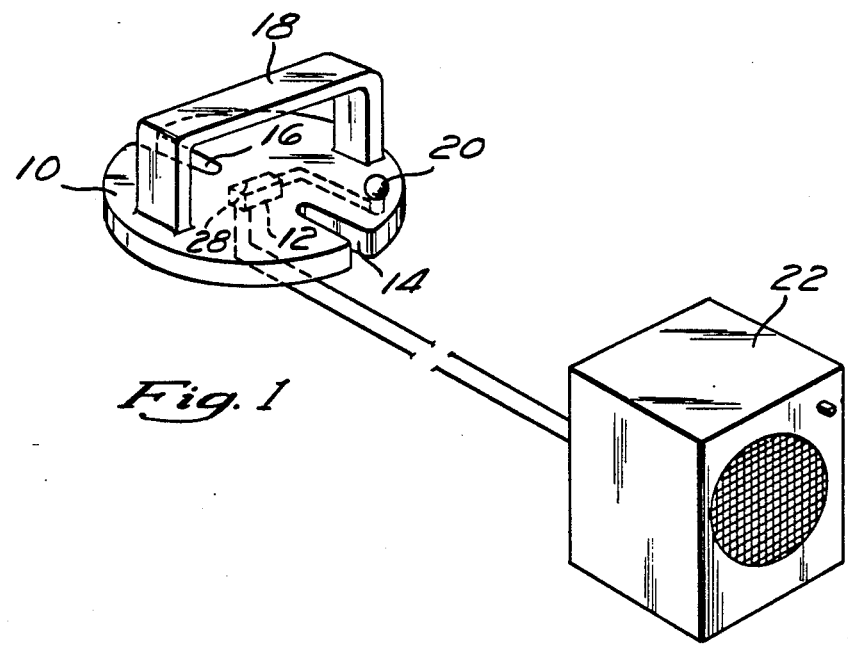
FIG. 1 is a perspective view of the invention.
Figure 2:
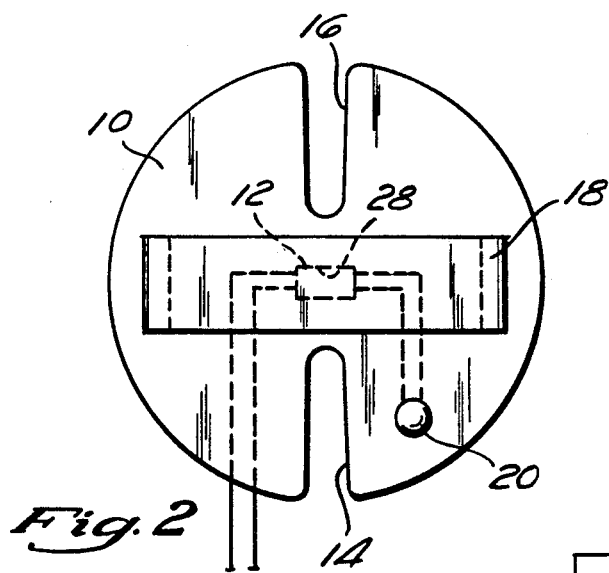
FIG. 2 is a plan view of the device of FIG. 1.
Figure 4:
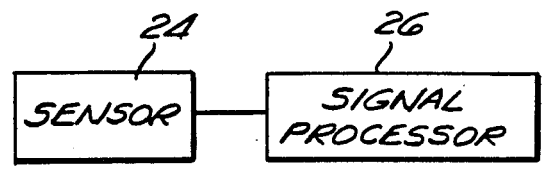
FIG. 4 is a block diagram of a blood flow detector disclosed.

FIG. 1 is a perspective view illustrating the novel structure of the invention. A plate 10 has a blood flow detector 12 imbedded therein between a pair of slots 14 and 16. The slots 14 and 16 extend away from the blood flow detector 12 and are generally in coaxial alignment with one another. FIG. 2, which is a plan view, illustrates a convenient configuration of the slots 14 and 16.

A handle 18 extends from the plate 10 to provide means for conveniently moving the plate over a patient's skin to locate an artery.

The blood flow detector 12 is connected to visual indicator means, such as a light 20. The blood flow detector 12 outputs a signal responsive to pulsatile changes in blood flow to cause the light 20 to produce visible light intermittently when the blood flow detector 12 is adjacent an artery in a patient.

The blood flow detector 12 is also connected to audio indicator means, such as loudspeaker 22, shown in FIG. 1. The blood flow detector 12 outputs a signal responsive to pulsatile changes in blood flow to cause the loudspeaker 22 to produce a sound, which trained personnel will understand as being indicative that the blood flow detector 12 is adjacent an artery.

The blood flow detector 12 preferably includes an ultrasonic sensor 24 and a signal processing unit 26 for determining a doppler effect responsive to blood flow. Such devices are well known in the art of medical instrumentation. The blood flow detector 12 may be model number 812, or 841, marketed by Park Electronic Laboratories of Beaverton, Oreg., or other similar device.

To use the invention, a medically trained person moves the plate 10 over the surface of a patient's skin in the vicinity of the artery whose exact location is to be ascertained. By observing the light 20 or by listening to the sound emitted from the loudspeaker 22, the operator locates the artery and aligns the slots 14 and 16 therewith. The intensity of the sound emitted from the loudspeaker 22 and the brightness of the light 20 increase as the blood flow detector 12 becomes closer to an artery.

Human arteries are typically 2-8 millimeters in diameter. Insertion of a catheter into an artery is ordinarily done through a hollow needle (not shown) having an outer diameter about the same as 18 gauge wire. The slots 14 and 16 have dimensions appropriate for holding an artery in position for puncturing an for allowing the needle to pass through into the artery.

After locating the artery, the operator presses the plate 10 against the patient's body with a moderate pressure to retain the artery in a stablized position in alignment with a selected slot 14 or 16. After the artery is located and the selected slot 14 or 16 is properly positioned relative to the artery, the operator or other medically trained person punctures the artery with a hollow needle (not shown) to withdraw blood, insert a catheter, or administer other medical treatment.

The plate 10 and handle 18 are preferably made of a transparent plastic material, but may satisfactorily be made of a metal or fiber-adhesive composite material or a combination including plastic, metal fiber-adhesive composite or other similar material.

The plate 10 may be formed as a single piece with a recess 28 therein for holding the blood flow detector 12, which may be secured within the recess 28 by any convenient means, such as an adhesive material.

Figure 3:
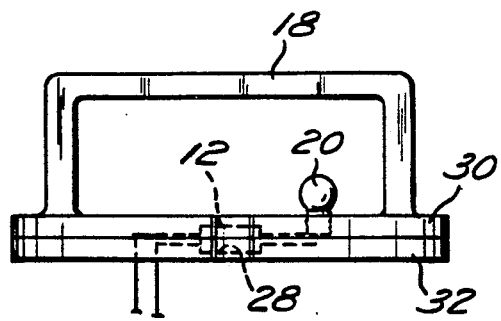
FIG. 3 is an elevation and view of the device shown in FIG. 2.

The plate 10 may be formed of an upper portion 30 and a lower portion 32 as shown in FIG. 3 with the blood flow detector being held between the upper portion 30 and lower portion 32.

Figure 5:
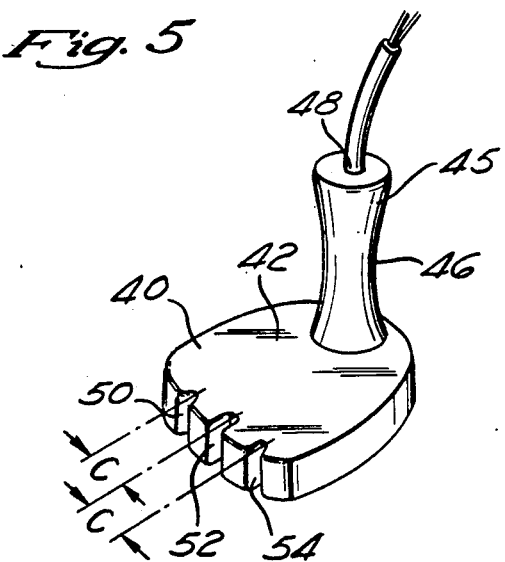
FIG. 5 is a top perspective view of an alternative embodiment of the device shown in FIGS. 1, 2, and 3.
Figure 6:
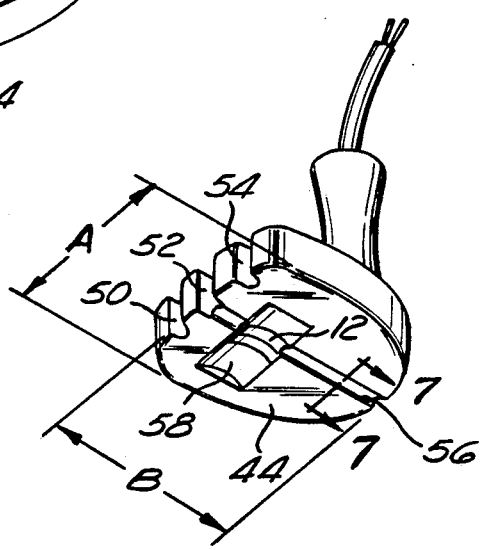
FIG. 6 is a bottom perspective view of the alternative embodiment.

FIGS. 5 and 6 depict an alternative embodiment of the invention having a foot-shaped plate 40 with an upper surface 42 and a lower surface 44. The plate 40 has a width depicted by a dimension A and a length depicted by a dimension B. By way of specific example, one embodiment constructed in accordance with this invention has a dimension A of approximately 1¼ inches and a dimension B of approximately 2¼ inches. Attached and centered on the top surface 42 proximate the rear of the plate 40 is a slender upright handle 45. This handle is essentially cylindrical in shape, however, in the middle of the cylinder is a necked down portion 46. The cylinder also has a circular opening 48 which extends through the center of the upright 45.

Located in the front of the plate 40 are three slots, the lateral slot 50, the central slot 52, and the medial slot 54. These slots are dimensioned to allow a hollow needle, catheter or cannula (not shown) to enter therein. The distance from the center line of one slot to the center line of an adjacent slot is depicted by a dimension C. In the specific example noted above, the dimension C is approximately equal to ⅜ inch.

Figure 7:
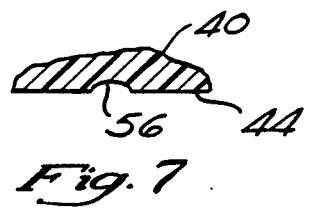
FIG. 7 is a cross-sectional view taken along the line 7—7 in FIG. 6.

Centered on the bottom surface 44 of the plate 40 is a rounded groove 56 which runs the length of the foot 40. The forward end of groove 56 lies in the central slot 52. (See FIG. 7). The radius of curvature of the groove 56 facilitates holding an artery in position in a centered position beneath surface 44 after the artery has been located. Also centered about the width of the plate 40 in the bottom surface 44 is a recess 58 which houses a blood flow detector 12. The blood flow detector 12 is also centered about the width of the plate 40. The wires or leads from the blood flow detector are encased within the body of the plate 40 and pass through the opening 48 in the upright 45. The wires are connected to a sensor 24 and signal processor 26 (see FIG. 3) to produce an audible or visual signal indicating when the plate is located adjacent to an artery in the patient's body. The intensity of the signal from the light 20 or the loudspeaker 22 is strongest when the groove 56 is positioned along the length of an artery.

In use medical personnel use the handle to move the plate 40 while searching for an artery. The necked down portion 46 prevents the medical personnel's fingers from slipping. Handle 45 can also be conveniently used to rotate the plate 40 by rolling the upright 45 between two of the fingers used to hold the upright. This convenient means for rotating the plate facilitates alignment of the groove 56 of the plate 40 adjacent the length of the artery in the body.

Once the artery is located, moderate pressure can be applied to the plate 40 which in turn holds the artery within the groove 56. Since the central slot 52 and the groove 56 are both centered about the lengthwise center of the plate 44, the artery is in a position for puncture. When the artery is directly beneath the groove 56, the artery also lies directly beneath the center slot 52. The artery is held by the end of the groove 56 which terminates at the slot 52 and is prevented from rolling away or shifting slightly with the insertion of the cannula, catheter or needle. Such shifting can prevent the desired puncturing of the artery and it is not uncommon that heretofore, medical personnel, after locating an artery still have difficulty in puncturing the blood vessel. Therefore, by using the central slot 52 to guide a cannula, catheter or needle (not shown), the artery is punctured and blood can then be drawn, a catheter can be inserted in the artery, or other necessary medical treatments can be performed.

The groove and slot arrangement is advantageous in that the artery is held in place.

For almost every artery in the human body there is an associated vein. The dimension C between adjacent slots 50, 52 and 54 corresponds to the anatomical spacing commonly found in the human body between the artery and the vein. The anatomical spacing between the artery and the vein differs for various portions of the body. For example, the spacing between veins and arteries in the groin area is larger than the spacing between veins and arteries in the arm. The spacing also varies with the sex and the weight of the individual. Thus, the dimension C, used in this invention depends on the personal characteristics of the patient and the area of the body where the invention is applied.

After locating the artery, medical personnel can puncture the corresponding vein by placing a cannula, catheter or needle in the medial slot 54, or the lateral slot 50. Piercing the skin through the medial slot 54, or the lateral slot 50 will pierce the vein which parallels the artery. Thus, the vein can be located easily and quickly by medical personnel without guesswork.

Although the present invention has been described with reference to a particular embodiment thereof, it will be understood by those skilled in the art that numerous modifications may be made without departing from the scope of the invention. Accordingly, all modifications and equivalence which are properly within the scope of the appended claims are included in the present invention.

What is claimed is:

1. Apparatus for positioning and thus aiding the puncturing of a predetermined artery and associated vein which are separated by a predetermined known distance, comprising:
   a base for placement against the skin of a patient at the location of said predetermined artery and vein;
   signal emitting means attached to said base for emitting a signal in response to pulsatile changes in blood flow to ascertain the relative position of said artery with respect to said base, and for thus positioning said base in alignment with said artery;
   first guide means for guiding a puncturing instrument substantially normally to said skin and into said artery when said base is in said alignment with said artery, said guide means being located on said base at a first position relative to said signal emitting means;
   second guide means for guiding a puncturing instrument substantially normally to said skin and into said vein and being located on said base at a second position relative to said signal emitting means, said second guide means being separated from said first guide means by said known distance.

2. Apparatus according to claim 1 wherein said signal emitting means includes doppler detector means for producing a signal indicative of pulsatile blood flow.

3. Apparatus according to claim 2, wherein said signal emitting means includes means responsive to said doppler detector means for emitting a signal to indicate that said signal emitting means is adjacent to an artery.

4. Apparatus according to claim 3, wherein said signal emitting means includes means for producing a visible light in response to said doppler detector means to indicate that said signal emitting means is adjacent to an artery.

5. Apparatus according to claim 4 wherein said signal emitting means includes means responsive to said doppler detector means for emitting a visible light to indicate that said signal emitting means is adjacent to an artery.

6. Apparatus according to claim 1 additionally comprising artery holding means comprising a groove on one side of said base, said groove being formed to hold an artery along its length by pressing said base against a human body with an artery adjacent the length of said groove.

7. Apparatus according to claim 6, wherein said means for emitting a signal produces a signal varying in intensity, the signal emitting means being positioned in said base to produce a more intense signal when the groove is positioned along the length of an artery.

8. Apparatus according to claim 7 wherein said first guide means include a first slot at the end of said groove.

9. Apparatus according to claim 7 wherein said second guide means comprises a second slot spaced said known distance from said first slot.

10. A method of locating and puncturing a vein which is spaced a predetermined known distance from an artery using an apparatus comprising:
    a base;
    signal emitting means attached to said base;
    first guide means for a puncturing instrument, said guide means being located on said base at a first position relative to said signal emitting means selected to guide said instrument into said artery; and
    second guide means for a puncturing instrument located on said base at a second position relative to said signal emitting means and separated from said first position by said known distance;
    said method comprising the steps of:
    placing said base of said apparatus against the skin of a patient at the location of the artery associated with the vein which is desired to be punctured;
    monitoring a signal from said signal emitting means indicative of the pulsatile changes in blood flow to ascertain the relative position of said artery with respect to said base and thereby aligning said base with said artery and in consequence aligning said first guide means with said artery and said second guide means with said vein; and
    puncturing said vein with a puncturing instrument in said second guide means.

* * * * *